(12) United States Patent
Weber et al.

(10) Patent No.: US 8,366,661 B2
(45) Date of Patent: Feb. 5, 2013

(54) MEDICAL DEVICE WITH EXPANDABLE BODY FOR DRUG DELIVERY BY CAPSULES

(75) Inventors: Jan Weber, Maastricht (NL); Steven P. Mertens, New Hope, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 37 days.

(21) Appl. No.: 12/953,698

(22) Filed: Nov. 24, 2010

(65) Prior Publication Data

US 2011/0152765 A1 Jun. 23, 2011

Related U.S. Application Data

(60) Provisional application No. 61/287,763, filed on Dec. 18, 2009.

(51) Int. Cl.
*A61M 31/00* (2006.01)
(52) U.S. Cl. .................................. 604/103.02
(58) Field of Classification Search ............ 604/103.02, 604/103.08, 57, 502, 509, 36; 623/1.44
See application file for complete search history.

(56) References Cited

U.S. PATENT DOCUMENTS

| | | |
|---|---|---|
| 5,893,840 A | 4/1999 | Hull et al. |
| 6,364,856 B1 | 4/2002 | Ding et al. |
| 7,364,585 B2 | 4/2008 | Weber |
| 7,572,625 B2 | 8/2009 | Davis et al. |
| 2006/0184237 A1 | 8/2006 | Weber et al. |
| 2007/0184085 A1 | 8/2007 | Radhakrishnan et al. |
| 2009/0043276 A1 | 2/2009 | Weber |
| 2009/0187238 A1 | 7/2009 | Weber et al. |

*Primary Examiner* — Nicholas Lucchesi
*Assistant Examiner* — Brooke Matney
(74) *Attorney, Agent, or Firm* — Kenyon & Kenyon LLP

(57) ABSTRACT

Medical devices using an expandable body to deliver a therapeutic agent. In one particular embodiment, the medical device comprises a tubular catheter and an inner expandable body (e.g., a scaffolding) contained within the catheter. The inner expandable body is connected to a core wire for advancing or retracting the inner body. The inner body may be advanced to exit out of the catheter or retracted to withdraw the inner body back into the catheter. This particular embodiment further comprises a sheath on the outside of the interior of the catheter. The sheath carries a plurality of capsules that contain a therapeutic agent. The therapeutic agent is delivered by pushing the core wire to advance the inner body, which expands against the sheath, causing the capsules on the sheath to be compressed against body tissue such that the therapeutic agent is released.

21 Claims, 4 Drawing Sheets

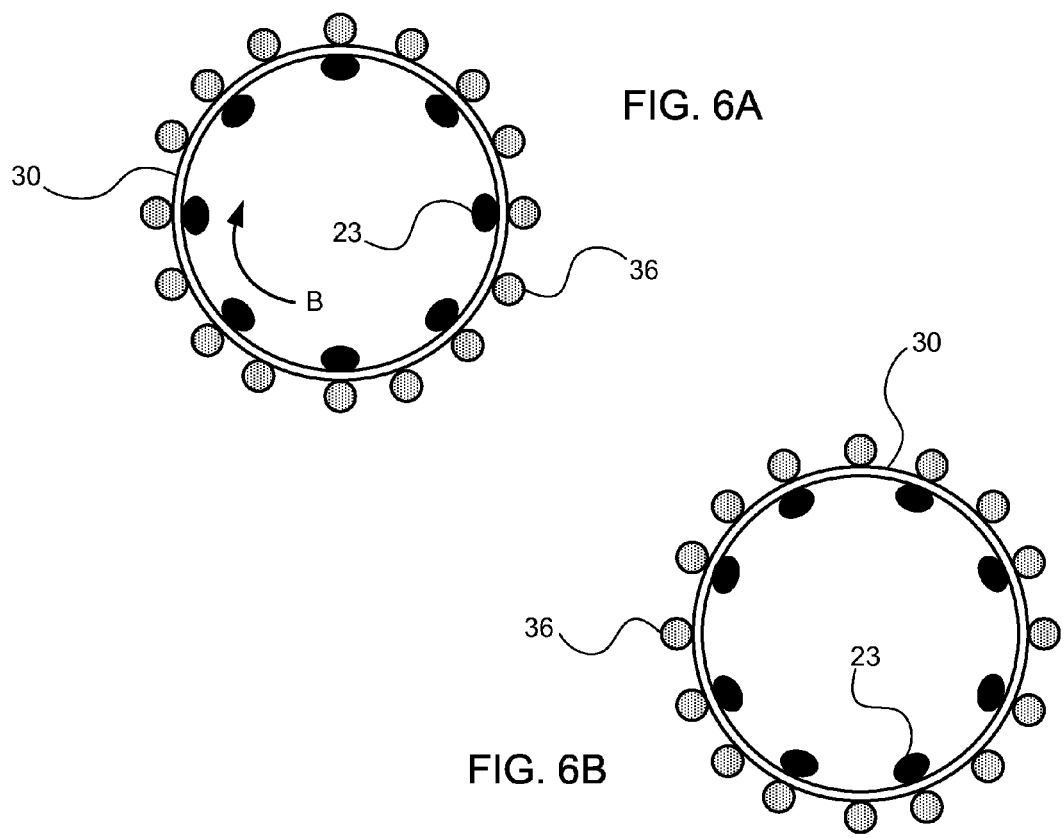
FIG. 6A
FIG. 6B
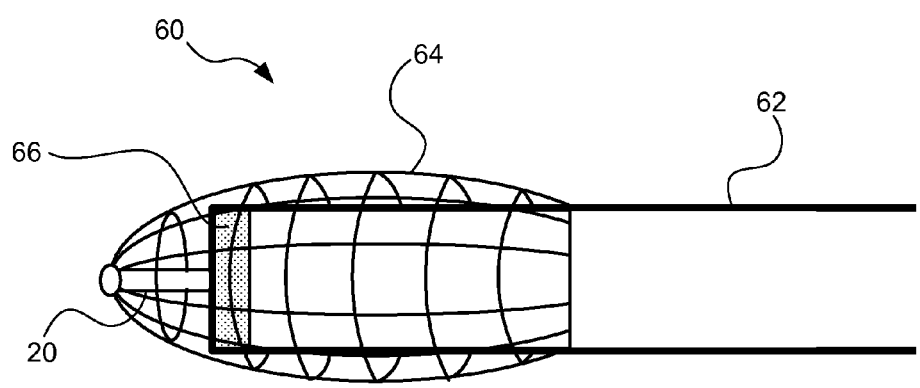
FIG. 7

MEDICAL DEVICE WITH EXPANDABLE BODY FOR DRUG DELIVERY BY CAPSULES

CROSS REFERENCE TO RELATED APPLICATION

The present application claims priority to U.S. provisional application Ser. No. 61/287,763 filed Dec. 18, 2009, the disclosure of which is incorporated herein by reference in its entirety.

TECHNICAL FIELD

The present disclosure relates to medical devices, such as balloon catheters or stents, for the delivery of therapeutic agents to body tissue.

BACKGROUND

Drugs are often delivered directly to target sites of diseased tissue in various contemporary medical procedures. This targeted delivery has proven to be an advantageous approach for treating numerous medical conditions. Using this targeted delivery approach, a controlled dose of the drug may be directly delivered to the target tissue while avoiding or minimizing exposure of other parts of the body to the drug. Also, greater amounts of drug may be delivered to the afflicted parts of the body. In one approach to localized drug delivery, catheter-based, minimally invasive medical procedures are used for deploying intravascular devices such as stents, grafts, or balloon catheters.

One of the problems that can be encountered with such techniques is premature release of the drug while the device is being inserted or deployed. For example, for intravascular devices coated with a drug, the flow of blood around the device can wash away the drug. In addition, insufficient or excessive contact time or pressure can result in inadequate or excessive drug delivery, or vessel injury. Therefore, there is a need for improved methods of delivering drugs to a target site.

SUMMARY

The medical devices disclosed herein can be used for delivering therapeutic agents. In some cases, the therapeutic agent is contained within capsules. The medical device may be designed to reduce the risk of prematurely releasing the therapeutic agent from the capsules.

In one embodiment, the present disclosure provides a medical device comprising: (a) a hollow tube having an interior space and an opening at the distal end; (b) a shaft within the hollow tube, the shaft moveable within the hollow tube along the longitudinal axis of the hollow tube; (c) an inner expandable body disposed within the hollow tube and connected to the shaft, the inner expandable body being moveable in and out of the hollow tube; (d) an outer expandable body disposed outside of the interior space of the hollow tube and connected to the inner expandable body, the shaft, or both; (e) a plurality of capsules carried by the outer expandable body; and (f) a therapeutic agent contained inside the capsules.

In another embodiment, the present disclosure provides a method for treating a patient, comprising: (a) providing a medical device comprising: a hollow tube having an interior space and an opening at the distal end; an inner expandable body disposed within the hollow tube, the inner expandable body being moveable in and out of the hollow tube; an outer expandable body disposed outside of the interior space of the hollow tube; a plurality of capsules carried by the outer expandable body; and a therapeutic agent contained inside the capsules; (b) inserting the hollow tube into a patient's body; (c) advancing the inner expandable body such that the inner expandable body at least partially exits the hollow tube; and (d) expanding the inner expandable body against the outer expandable body to release the therapeutic agent from the capsules.

In another embodiment, the present disclosure provides a method for treating a patient, comprising: (a) using a medical device comprising: a hollow tube having an interior space and an opening at the distal end; an inner expandable body disposed within the hollow tube, the inner expandable body being moveable in and out of the hollow tube; an outer expandable body disposed outside of the interior space of the hollow tube; and a therapeutic agent carried by the outer expandable body; (b) inserting the hollow tube into a patient's body; (c) advancing the inner expandable body relative to the distal end of the hollow tube such that the inner expandable body at least partially exits the hollow tube; (d) expanding the inner expandable body against the outer expandable body a first time to deliver a first portion of the therapeutic agent; (e) collapsing the inner expandable body and repositioning the inner expandable body; and (f) expanding the inner expandable body against the outer expandable body a second time to deliver a second portion of the therapeutic agent.

BRIEF DESCRIPTION OF THE DRAWINGS

FIG. 1A shows a side view of the medical device. FIG. 1B shows a see-through side view of the medical device. FIG. 1C shows a transverse cross-section view of the medical device.

FIG. 2A shows a side view and FIG. 2B shows a see-through side view.

FIG. 6A shows a transverse cross-section view of the medical device shown in FIG. 2A taken at arrow A. FIG. 6B shows the same view after slightly rotating the nitinol basket.

FIG. 7 shows a side view of a medical device according to another embodiment of the present disclosure.

DETAILED DESCRIPTION

Figure 1A:
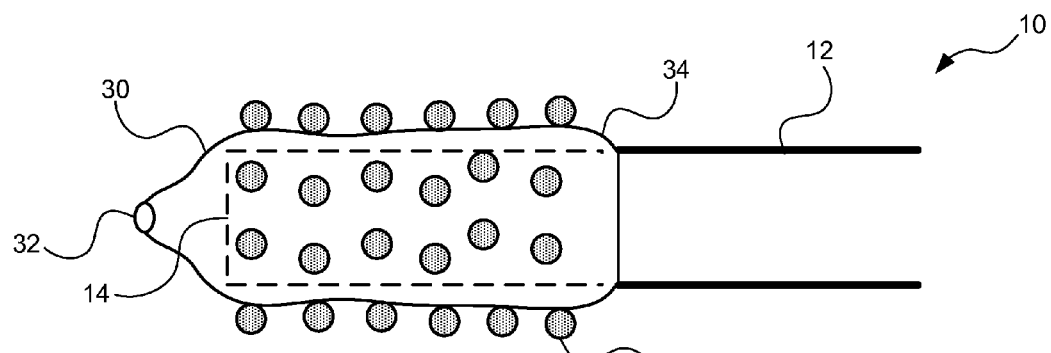
FIGS. 1A-C show a medical device according to an embodiment of the present disclosure.

In one embodiment, a medical device of the present disclosure comprises a hollow tube that functions to guide and/or deliver the inner and outer expandable bodies (described below) to the target site in the patient's body. For example, the hollow tube may be a vascular catheter, such as a guide catheter or an access catheter. Contained within the hollow tube is a shaft that is moveable within the hollow tube along its longitudinal axis. Also contained within the hollow tube is an inner expandable body that is connected to the shaft. The inner expandable body can be moved in and out of an opening at the distal end of the hollow tube. The medical device further comprises an outer expandable body disposed on the outside of the interior space of the hollow tube and connected to the inner expandable body and/or the shaft. The outer expandable body carries a therapeutic agent.

The inner expandable body is capable of being radially expanded, but is radially constrained within the hollow tube for delivery to the target site. The distal end of the hollow tube has an exit opening to allow the inner expandable body to exit the hollow tube. The inner expandable body may be advanced out of the exit opening of the hollow tube and retracted back into the hollow tube. As used herein, the terms "advanced" and "refracted," when referring to the inner expandable body or the outer expandable body, refers to the relative motion between the inner or outer expandable body and the hollow tube. Advancing the expandable body (inner or outer) means that the expandable body moves distally in relation to the hollow tube; and retracting the expandable body means that the expandable body moves proximally in relation to the hollow tube. Advancing the expandable body may be carried out by moving the expandable body distally, or by moving the hollow tube proximally, or a combination of both. Likewise, retracting the expandable body (inner or outer) may be carried out by moving the expandable body proximally, or by moving the hollow tube distally, or a combination of both.

The inner expandable body can have a variety of different dimensions, depending upon the particular application. For vascular applications, the inner expandable body can have an elongate, cylinder-like shape with a length suitable for extending across a vascular lesion (e.g., an arterial plaque) and a diameter corresponding to the lumen of a blood vessel in the body. For example, the inner expandable body can have dimensions similar to balloons or stents used in treating arteries, such as the coronary arteries, carotid arteries, or other peripheral arteries in the body. For example, the inner expandable body may have a length in the range of 5 mm to 20 cm, and an expanded diameter in the range of 2 mm to 20 mm, but other dimensions are also possible. In some cases, there is at least one distal point on the inner expandable body where the inner expandable body is narrower in diameter (e.g., 1-4 mm narrower) than a more proximal point on the inner expandable body when the inner expandable body is expanded. This feature can be beneficial where the device needs to accommodate a tapering in the diameter of the blood vessel towards the distal end, such as when being used in a relatively longer blood vessel (e.g., a femoral artery).

In certain embodiments, the inner expandable body may be a scaffolding comprising one or more filaments. As used herein, "filament" means any suitable strut or wire-like structure that can be used to make baskets, stents, coils, meshes, cages, nets, etc. The transverse cross-section of the filament can have any suitable shape, including circular, rectangular, square, or oval. More than one filament may be used to make the scaffolding. The one or more filaments are formed of materials that provide the scaffolding with the desired structural characteristics (e.g., flexibility or elasticity). Such materials include polymers and metals that are biocompatible or otherwise known to be used in medical devices for insertion in a patient's body. In some cases, the filament(s) comprise a biocompatible metal, such as nitinol, platinum, stainless steel (e.g., 316 L), or a mixture thereof.

In some cases, the scaffolding is self-expanding, which can be provided by designing the scaffolding to be biased towards the expanded configuration. For example, the self-expanding scaffolding can be made using shape memory materials such as nitinol, stainless steel, other super-elastic metal alloys, or polymeric materials. In some cases, the medical device may use an actuating mechanism to expand the scaffolding. Examples of such actuation mechanisms include mechanical (e.g., using levers, wires, strings, pulleys, plungers, balloons, etc.), electrical, electro-mechanical, chemical, pneumatic, or hydraulic mechanisms.

In certain embodiments, the inner expandable body is a balloon. For example, in vascular applications, the balloon used in the medical device may be similar to angioplasty balloons or stent deployment balloons. The medical device may use any suitable mechanism for inflating the balloon.

The medical device further comprises a shaft contained within the hollow tube and axially moveable therein. The shaft functions to move the inner expandable body within the hollow tube and in/out of the exit opening of the hollow tube. As such, the shaft is connected to the inner expandable body. In some cases, the shaft is permanently connected to the inner expandable body. As used herein, "permanently connected" means that the two parts (e.g., inner expandable body and the shaft) are connected in a manner such that they stay connected for at least the duration of the deployment and withdrawal of the medical device from the patient's body. As such, the inner expandable body is not intended to be implanted in the patient's body. Rather, after deployment, the inner expandable body is designed to be retracted back into the hollow tube and withdrawn from the body.

The shaft can be any elongate structure having sufficient stiffness to advance the inner expandable body, while having sufficient flexibility to allow navigation to the target site in the patient's body. For example, the shaft may be similar to guidewires used in deploying stents or angioplasty balloons.

The medical device further comprises an outer expandable body disposed outside of the interior space of the hollow tube and connected to the inner expandable body, the shaft, or both. In some cases, the outer expandable body is permanently connected to the inner expandable body, the shaft, or both. The outer expandable body is provided in a compact configuration to reduce its radial profile, which can facilitate insertion of the medical device into the patient's body and delivery to the target site. For example, the outer expandable body may be in a close-fitting configuration around the hollow tube. The outer expandable body is designed to become expanded at least in the radial direction by the inner expandable body when the inner expandable body exits out of the hollow tube. Accordingly, the outer expandable body can be any suitable structure capable of being expanded by the inner expandable body.

Being outside of the interior space of the hollow tube can mean that the outer expandable body is outside of the hollow tube or within the wall of the hollow tube. For example, there may be an annular space within the wall of the hollow tube for containing the outer expandable body, as described in the commonly-assigned U.S. Patent Application Publication No. 2006/0184237 (Weber et al., "Method of Incorporating a Drug-Eluting External Body in a Medical Appliance and a Self-Expanding Stent Including a Drug-Eluting External Body May Have an Annular Space"), which is incorporated by reference herein.

In some cases, the outer expandable body is a scaffolding, such as the scaffolding structures described above for the inner expandable body. For vascular applications, using a scaffolding as the outer expandable body may be beneficial for reducing interruption to the flow of blood as the outer expandable body is expanded inside the blood vessel.

In some cases, the outer expandable body is a sheath that provides a more continuous covering (e.g., the sheath may be a polymer sheet, membrane, or sleeve to cover over the inner expandable body). The sheath may undergo radial expansion by being unfolded from a folded configuration, by being stretched out, or by undergoing any other suitable type of deformation.

In some cases, the outer expandable body is elastically deformable (i.e., the deformation is reversible) and is designed to have a bias towards the compact configuration (i.e., configuration prior to being radially expanded). In such cases, after being expanded, the outer expandable body will revert to its compact configuration when the expanding force is removed. For example, in cases where the outer expandable body is a scaffolding, the filaments that make up the scaffolding may be configured to bias the shape of the scaffolding towards the compact configuration. In another example, in cases where the outer expandable body is a sheath, the sheath may be made of an elastic polymeric material, such as a silicone elastomer or a thermoplastic elastomer. Examples of thermoplastic elastomers include thermoplastic polyurethanes, thermoplastic polyesters, and thermoplastic polyamides such as polyether block amide (e.g., PEBAX®).

The outer expandable body may be designed to cover over the inner expandable body as the inner expandable body is moved out of the hollow tube. This may require that the outer expandable body move or be extended along the hollow tube to follow the advancing movement of the inner expandable body. In some cases, the outer expandable body is slidable with respect to the hollow tube. This allows the outer expandable body to advance distally as the inner expandable body is moved out of the hollow tube and/or retracted proximally as the inner expandable body is withdrawn back into the hollow tube. In some cases, the outer expandable body is expandable along the longitudinal axis of the hollow tube. For example, the outer expandable body may having accordian-type pleatings that unfold to longitudinally extend the outer expandable body and allow it to cover over the inner expandable body.

A therapeutic agent is carried by the outer expandable body. The outer expandable body can carry the therapeutic agent in any suitable manner. In some cases, the therapeutic agent is applied as a coating on the outer expandable body. For example, the therapeutic agent coating may be similar to those used in drug-coated stents or balloon catheters.

In some cases, a plurality of capsules are carried by the outer expandable body and the therapeutic agent is contained in the capsules. In this arrangement, the capsules are located outside the interior space of the hollow tube. If the capsules were to be carried on the inner expandable body inside the interior space of the hollow tube, the capsules may prematurely rupture due to compression against the hollow tube and/or shear forces as the inner expandable body is advanced within the hollow tube. By having the capsules located on the outer expandable body, the risk of premature release of the therapeutic agent from the capsules is reduced.

Because the capsules are carried on the outer expandable body, the capsules may be designed to release the therapeutic agent at contact pressures lower than what would be possible if the capsules were located inside the interior space of the hollow tube, where they could be subjected to compression against the hollow tube and/or shear forces that could cause premature release of the therapeutic agent. Table 1 below shows the results of a finite element analysis performed on a balloon-artery simulation (with the artery being modeled as an elastic body) to determine contact pressures of the balloon against the artery wall at various inflation pressures and balloon diameters. The balloon was modeled as a polyamide 12 balloon having a 3 mm nominal diameter. The artery was modeled as a 3 mm diameter straight vessel. Based on these results, in certain embodiments, the capsules are designed to release the therapeutic agent at a contact pressure of 0.25 MPa (megapascals) or less; or 0.125 MPa or less; or 0.05 MPa or less; and in some cases, in the range of 0.05-0.25 MPa.

TABLE 1

Balloon-artery contact pressure comparisons.

| Pressure (MPa) | Simulation 1 | | Simulation 2 | |
|---|---|---|---|---|
| | Balloon diameter (mm) | Contact pressure (MPa) | Balloon diameter (mm) | Contact pressure (MPa) |
| 0.8 | 3.04 | 0.0000 | 3.04 | 0.000 |
| 1.1 | 3.11 | 0.0021 | 3.11 | 0.012 |
| 1.4 | 3.19 | 0.0029 | 3.19 | 0.024 |
| 1.7 | 3.29 | 0.0039 | 3.27 | 0.062 |
| 2.0 | 3.40 | 0.0064 | 3.34 | 0.126 |

The capsules may be microspheres, liposomes, micelles, vesicles, or any of other various drug delivery particles that are known to be used for containing a therapeutic agent. For example, the capsules may be those described in commonly-assigned U.S. Patent Application Publication No. 2009/0043276 (Drug Delivery Device, Compositions and Method Relating Thereto) or U.S. Pat. No. 7,364,585 (Medical Devices Comprising Drug-Loaded Capsules for Localized Drug Delivery), both of which are incorporated by reference herein in their entirety. The capsules may have any of various shapes, including spherical shapes or irregular shapes. The capsules may be formed by the layer-by-layer self-assembly technique described in U.S. Patent Application Publication No. 2009/0043276 or U.S. Pat. No. 7,364,585, both of which are incorporated by reference herein in their entirety. In some cases, the shell of the capsules may comprise any suitable polymer material that is biocompatible or otherwise known to be used in drug delivery particles. The polymer material may be biodegradable or bioerodible. Other suitable materials include ionic polymers, polyelectrolytes, biologic polymers, and lipids.

The capsules contain a therapeutic agent and are designed to release the therapeutic agent when compressed against body tissue. As such, the capsules may open, rupture, or otherwise become more permeable to the therapeutic agent when subject to mechanical stress, resulting in the release of the therapeutic agent. Various properties of the capsules may be adjusted to provide this feature, including the capsule shell thickness, the diameter, the number of shells, or the composition of the shells.

The capsules may be carried on the outer expandable body in any suitable manner. For example, the capsules may be embedded or adhered to a coating (e.g., a hydrogel coating) on the outer expandable body; or the capsules may be adhered to the outer expandable body via an adhesive; or the capsules may be held on the outer expandable body by magnetic attraction (e.g., the capsules may contain ferromagnetic particles); or the capsules may be held on the outer expandable body by mechanical means (e.g., within folds, pockets, grooves, wells, or indentations in the outer expandable body).

Figure 5A:
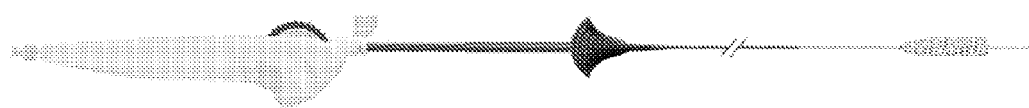
FIG. 5A shows an Epic® stent system (Boston Scientific).
Figure 5B:
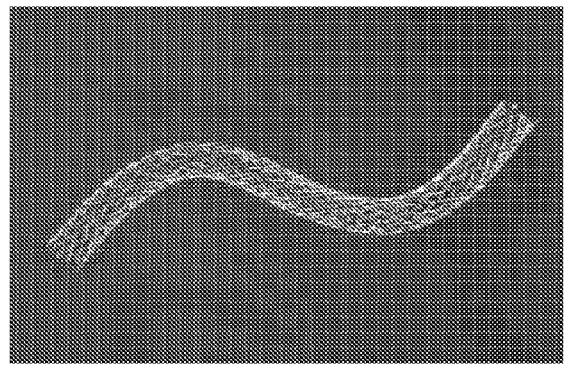
FIG. 5B shows the stent portion of the Epic® stent system.

A specific example of a medical device according to a particular embodiment of the present invention is shown in FIGS. 1A (side view), 1B (see-through side view), and 1C (transverse cross-section view). Medical device 10 includes a flexible, vascular guide catheter 12 (representing a hollow tube) that contains a flexible core wire 20 (representing a shaft) made of stainless steel. Catheter 12 is similar to the catheter used in an Epic® stent system (Boston Scientific; see FIG. 5A), which uses a 6 French, braided, Vestamid® L2101 (polyamide) catheter. Catheter 12 has an opening at its distal end 14. Also contained within catheter 12 is a self-expanding basket 22 (representing an inner expandable body) made of nitinol. Nitinol basket 22 is contained inside catheter 12 in a compact configuration. Nitinol basket 22 may have, for example, a length of 5-20 mm and may be made of wire-like filaments similar to an Epic® nitinol stent (Boston Scientific; see FIG. 5B).

Core wire 20 can be moved back and forth within catheter 12. Self-expanding nitinol basket 22 is attached to core wire 20 at the proximal end 38 of nitinol basket 22. Nitinol basket 22 can be attached to core wire 20 by inserting the proximal end of nitinol basket 22 over core wire 20 into a polyester heat-shrink tubing. Application of heat to the heat-shrink tubing (e.g., 125° C. for 10 seconds) will shrink the tubing around the proximal end of nitinol basket 22 and secure it to core wire 20.

On the outside of catheter 12 is an outer expandable body in the form of an elastic, low durometer, polyurethane sheath 30 in a form-fitting configuration around catheter 12. At its distal end 32, sheath 30 is attached to the distal end of core wire 20. At its proximal end 34, sheath 30 is slidable along catheter 12. Sheath 30 has a hydrogel coating for carrying a plurality of capsules 36 on sheath 30. Capsules 36 contain a therapeutic agent.

Figure 2A:
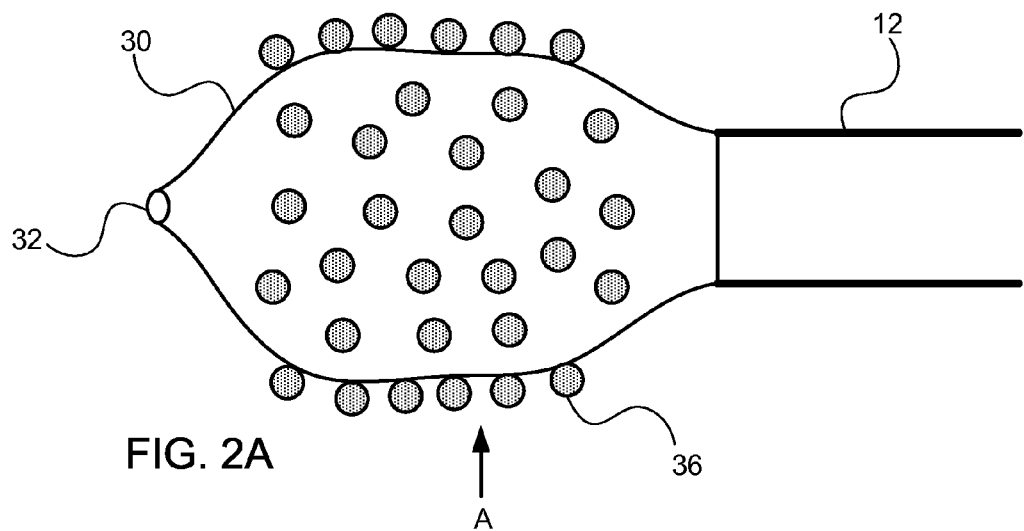
FIGS. 2A and 2B show the medical device of FIGS. 1A-C with the inner nitinol basket advanced out of the guide catheter.

In an example procedure, catheter 12 is directed into a patient's artery (e.g., carotid or coronary artery) by a suitable method (e.g., femoral artery approach) and guided to the target site. As seen in FIGS. 2A (side view) and 2B (see-through side view), at the target site, nitinol basket 22 is made to exit out of the distal end 14 of catheter 12. Nitinol basket 22 may be advanced by pushing core wire 20 distally relative to catheter 12, or by pulling catheter 12 relative to nitinol basket 22, or a combination of both.

As nitinol basket 22 exits catheter 12, polymer sheath 30 is also carried forward by its distal attachment 32 to core wire 20. Further advancement of polymer sheath 30 beyond the tip of catheter 12 may be limited by a position-fixing means (e.g., by a stop ring at the distal end of catheter 12). As nitinol basket 22 exits the distal end 14 of catheter 12, nitinol basket 22 self-expands and pushes out against polymer sheath 30. As polymer sheath 30 expands outward, capsules 36 are compressed against the arterial wall, causing capsules 36 to deform and release the therapeutic agent. In an alternate embodiment, sheath 30 may have openings (e.g., holes, slits, perforations, etc.) at its distal portion to allow for the flow of blood through sheath 30.

Figure 3:
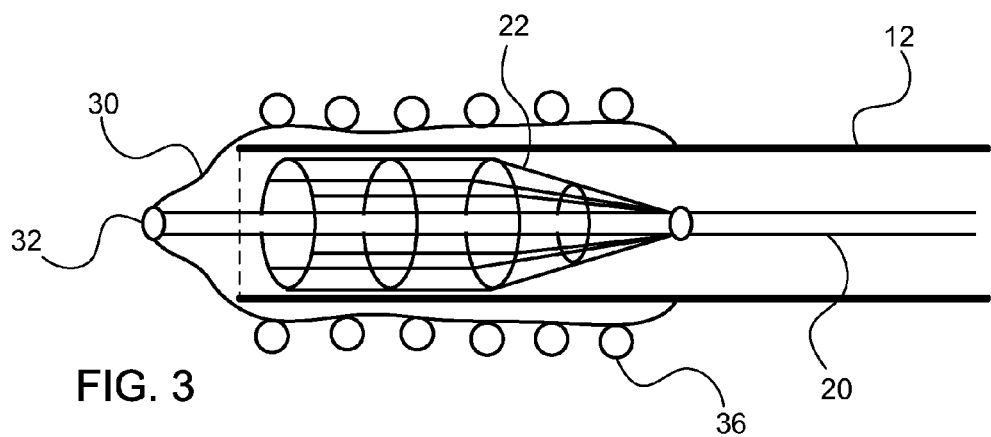
FIG. 3 (see-through side view) shows the medical device of FIGS. 1A-C after deployment with the inner nitinol basket retracted back into the catheter.

As seen in FIG. 3 (see-through side view), after the therapeutic agent is released (with capsules 36 shown being depleted of the therapeutic agent), nitinol basket 22 is retracted back into catheter 12 by pulling core wire 20, or pushing catheter 12, or a combination of both. As nitinol basket 22 returns back into catheter 12, nitinol basket 22 collapses back into its compact configuration.

Figure 1B:
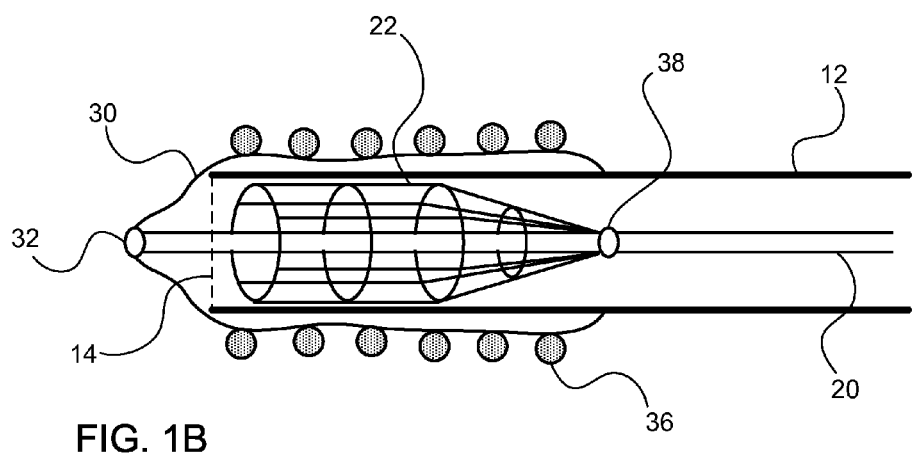
Figure 1C:
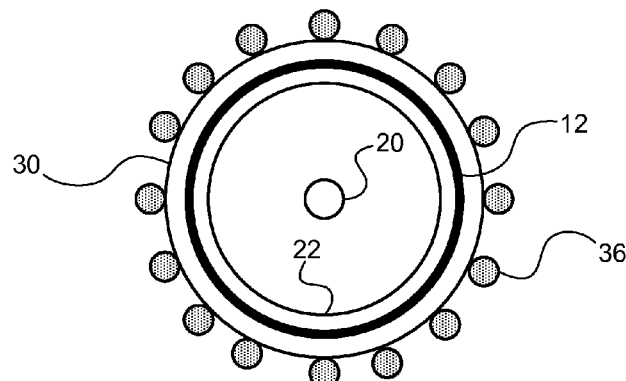
Figure 4:
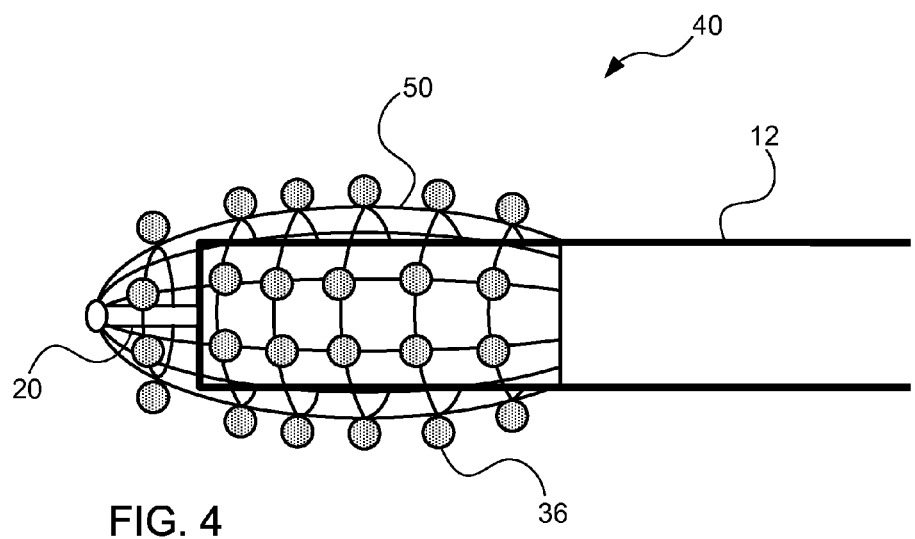
FIG. 4 shows a side view of a medical device according to another embodiment of the present disclosure.

Another specific example of a medical device according to a particular embodiment of the present invention is shown in FIG. 4 (side view). In this example, medical device 40 includes a guide catheter 12 and a core wire 20. Contained within catheter 12 is a self-expanding nitinol basket (not shown) that is attached to core wire 20. This inner nitinol basket is contained inside catheter 12 in a compact configuration. The inner nitinol basket may have a structure and dimensions similar to nitinol basket 22 shown in FIGS. 1A-C above. On the outside of catheter 12 is an outer nitinol basket 50 (representing an outer expandable body) that is elastically in a form-fitting configuration around the distal tip of catheter 12. Outer nitinol basket 50 is designed to be expanded by the inner nitinol basket. For example, the inner nitinol basket may be similar to a Boston Scientific Epic® stent having relatively thicker wire struts, while the outer nitinol basket may be similar to a Boston Scientific Epic® stent having relatively thinner wire struts.

At its distal end, outer nitinol basket 50 is attached to the distal end of core wire 20. At its proximal end, outer nitinol basket 50 is slidable along catheter 12. Capsules 36 containing a therapeutic agent are adhered onto outer nitinol basket 50 by an adhesive. In operation, the inner nitinol basket is made to exit the catheter, whereupon the inner nitinol basket expands against outer nitinol basket 50. Compression of capsules 36 against the arterial wall causes the release of the therapeutic agent. After deployment, the inner nitinol basket is retracted back into catheter 12 and outer nitinol basket 50 elastically returns to its compact configuration around catheter 12.

The medical devices of the present invention may also be designed for multiple treatments and/or deployments within the patient's body without having to withdraw the medical device from the patient's body to replenish the supply of therapeutic agent. For example, for intravascular use, the medical device may be designed to treat two or more separate lesions within a blood vessel in a single catheterization procedure. The multiple deployments of the outer expandable body may be performed with or without retracting the outer expandable body between deployments.

In certain embodiments, the outer expandable body carries two or more different types of capsules. Using different types of capsules allows for different release of the therapeutic agent. For example, the different types of capsules may be designed to release the therapeutic agent at different compressive forces. For example, an outer expandable body may have one set of capsules that bursts open at 1 atm compressive pressure and another set of capsules that bursts open at 3 atm compressive pressure. When the outer expandable body is expanded under controlled pressure (e.g., by a balloon as the inner expandable body), one target site can be treated by expansion at 1.5 atm pressure, which will burst open the first set of capsules, but leave the 3 atm capsules intact. The outer expandable body can then be retracted and returned to its compact configuration. Then, after re-positioning at another target site, the outer expandable body can be expanded again, this time at 4 atm pressure, thus bursting open the remaining set of capsules. The different capsules may contain the same therapeutic agent or different therapeutic agents.

Figure 2B:
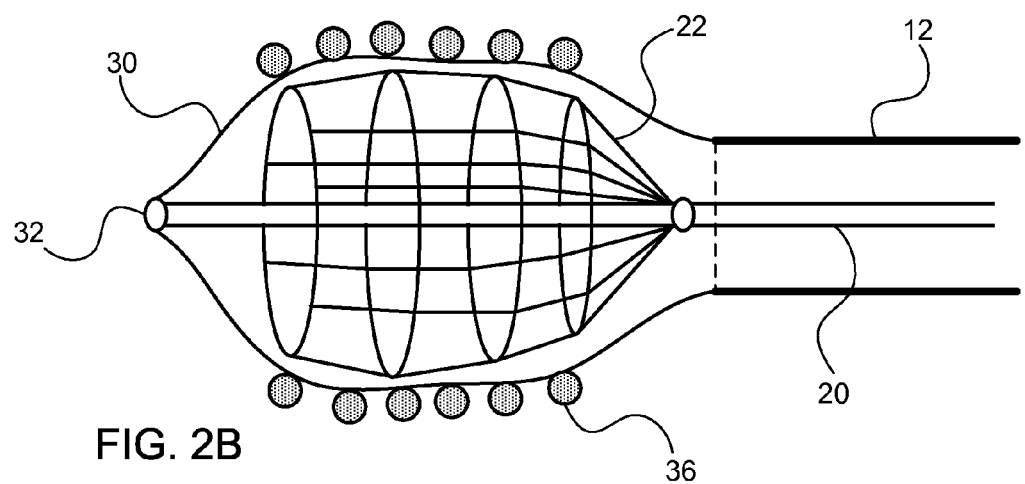

The medical devices of the present invention can be used to apply different portions of the outer expandable body in multiple deployments. This can allow for multiple applications of the therapeutic agent carried by the outer expandable body (e.g., as a coating or contained within capsules). In some cases, this can be performed by advancing the inner expandable body in such a way that different portions of the outer expandable body are made to exit out of the hollow tube for different deployments. For example, referring back to FIGS. 2A and 2B, instead of fully advancing nitinol basket 22 out of catheter 12, nitinol basket 22 can be advanced only halfway out of catheter 12 such that only the distal half of sheath 30 is expanded against the body tissue. As a result, only the capsules 36 on the distal half portion of sheath 30 are consumed in this deployment. In the next deployment, after retracting nitinol basket 22 and sheath 30, catheter 12 is re-positioned and nitinol basket 22 is fully advanced out of catheter 12 such that all of sheath 30 is expanded out. As a result, the remaining capsules 36 on the proximal half of sheath 30 are applied in the second deployment.

In some cases, multiple applications of the therapeutic agent can be performed by rotating (on the long axis) the inner expandable body between deployments. For example, referring back FIGS. 2A and 2B, the inner nitinol basket 22 can be slightly rotated between deployments to apply different sets of capsules 36. This is illustrated in FIGS. 6A and 6B, which are transverse cross-section views of the medical device shown in FIG. 2A taken at arrow A. FIG. 6A (catheter 12 and core wire 20 not shown) shows the first deployment, where the struts 23 of inner basket 22 compress against the first set of capsules 36. In the next deployment, after retracting nitinol basket 22 and sheath 30, catheter 12 is re-positioned and nitinol basket 22 is slightly rotated (in the direction of arrow B) before being advanced out of catheter 12 and expanded again. As shown in FIG. 6B, in this second deployment, the struts 23 of inner basket 22 compress against a different set of capsules 36.

Multiple deployments can also be facilitated by providing a coating applicator to the distal end of the hollow tube. The coating applicator contains a therapeutic agent and applies a coating of the therapeutic agent onto the outer expandable body as the outer expandable body moves over the distal end of the hollow tube. An example of a coating applicator is described in U.S. Patent Application Publication No. 2009/0187238 (Boston Scientific SciMed; "System and Method for Deploying Self-Expandable Medical Device With Coating"). As explained therein, such coating applicators may employ high viscosity gels, ball assemblies, O-rings, etc. For example, the coating applicator may be a hollow ring that contains the therapeutic agent. The hollow ring has an outer surface with holes in the outer surface to allow transfer of the therapeutic agent onto the outer expandable body. In another example, the coating applicator may have a housing containing spherical balls that apply the coating as the outer expandable body passes over. In another example, the coating applicator may comprise a gel that is sheared off and coated onto the outer expandable body. By using such coating applicators, after deployment, additional therapeutic agent may be applied as a coating onto the outer expandable body in preparation for the next deployment. For example, FIG. 7 shows a medical device 60 having a guide catheter 62 and a core wire 20 contained within guide catheter 62. At the distal tip of catheter 62 is a coating applicator 66.

Also contained within catheter 62 is a self-expanding inner nitinol basket (not shown) that is attached to core wire 20. The inner nitinol basket is contained inside catheter 62 in a compact configuration. On the outside of catheter 62 is an outer nitinol basket 64 (representing an outer expandable body) that is elastically in a form-fitting configuration around the distal tip of catheter 62. Outer nitinol basket 64 has a coating containing a therapeutic agent.

In operation, outer nitinol basket 64 is deployed and some of the therapeutic agent coating is applied onto the body tissue. As the outer nitinol basket 64 is retracted back onto catheter 62, coating applicator 66 replenishes the therapeutic agent coating on outer nitinol basket 64. In the next deployment, as outer nitinol basket 64 is advanced forward, coating applicator 66 further replenishes the therapeutic agent coating on outer nitinol basket 64.

The medical devices disclosed herein may further comprise other components. For example, the above-described medical device assembly may be contained inside a larger, wider bore catheter. The medical devices disclosed herein may be used in a variety of body structures, cavities, or lumens, including the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

The therapeutic agent used in the present invention may be any pharmaceutically acceptable agent (such as a drug), a biomolecule, a small molecule, or cells. Exemplary drugs include anti-proliferative agents such as paclitaxel, sirolimus (rapamycin), tacrolimus, everolimus, biolimus, and zotarolimus. Exemplary biomolecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, and lipids and compounds have a molecular weight of less than 100 kD. Exemplary cells include stem cells, progenitor cells, endothelial cells, adult cardiomyocytes, bone marrow cells, and smooth muscle cells. Other therapeutic agents that may be used in the present invention include those listed in U.S. Pat. No. 7,572,625 (Davis et al., "Medical devices coated with drug carrier macromolecules"), which is incorporated by reference herein. Any of the therapeutic agents may be combined to the extent such combination is biologically compatible.

The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention.

We claim:

1. A medical device comprising:
   a hollow tube having an interior space and an opening at the distal end;
   a shaft within the hollow tube, the shaft moveable within the hollow tube along the longitudinal axis of the hollow tube;
   an inner expandable body disposed within the hollow tube and connected to the shaft, the inner expandable body being moveable in and out of the hollow tube;
   an outer expandable body disposed over an outer circumferential surface of the hollow tube and connected to the inner expandable body, the shaft, or both;
   a plurality of capsules carried by the outer expandable body; and
   a therapeutic agent contained inside the capsules.

2. The device of claim 1, wherein the shaft is permanently connected to the inner expandable body.

3. The device of claim 1, wherein the inner expandable body expands when moved out of the hollow tube.

4. The device of claim 3, wherein the inner expandable body expands against the outer expandable body when the inner expandable body moves out of the hollow tube.

5. The device of claim 1, wherein the inner expandable body is a scaffolding.

6. The device of claim 5, wherein the scaffolding is formed of one or more metal filaments.

7. The device of claim 5, wherein the scaffolding is self-expandable.

8. The device of claim 1, wherein the outer expandable body is in a compact configuration around the hollow tube and has an elastic bias towards the compact configuration.

9. The device of claim 1, wherein the outer expandable body is a polymer sheath.

10. The device of claim 1, wherein the outer expandable body is a scaffolding.

11. The device of claim 1, wherein at least two different types of capsules are carried by the outer expandable body, wherein at least one type of capsules release the therapeutic agent at a first compressive force, and wherein at least another type of capsules release the therapeutic agent at a second compressive force that is different from the first compressive force.

12. The device of claim 1, wherein the therapeutic agent contained inside the capsules is a first therapeutic agent, and further comprising a coating applicator at the distal end of the hollow tube, the coating applicator being adapted to apply a second therapeutic agent onto the outer expandable body as the outer expandable body passes over the coating applicator.

13. The device of claim 1, wherein the capsules are adapted to release the therapeutic agent at a contact pressure of 0.125 MPa or less.

14. A method of treating a patient, comprising:
(a) using a medical device comprising:
a hollow tube having an interior space and an opening at the distal end;
an inner expandable body disposed within the hollow tube, the inner expandable body being moveable in and out of the hollow tube;
an outer expandable body disposed over an outer circumferential surface of the hollow tube;
a plurality of capsules carried by the outer expandable body; and
a therapeutic agent contained inside the capsules;
(b) inserting the hollow tube into a patient's body;
(c) advancing the inner expandable body such that the inner expandable body at least partially exits the hollow tube; and
(d) expanding the inner expandable body against the outer expandable body to release the therapeutic agent from the capsules.

15. The method of claim 14, wherein the inner expandable body self-expands when exiting the hollow tube.

16. The method of claim 14, further comprising retracting the inner expandable body back into the hollow tube.

17. The method of claim 16, wherein the outer expandable body is in a compact configuration around the hollow tube prior to deployment, and wherein the outer expandable body elastically returns to the compact configuration after deployment.

18. A method of treating a patient, comprising:
(a) using a medical device comprising:
a hollow tube having an interior space and an opening at the distal end;
an inner expandable body disposed within the hollow tube, the inner expandable body being moveable in and out of the hollow tube;
an outer expandable body disposed over an outer circumferential surface of the hollow tube; and
a therapeutic agent carried by the outer expandable body;
(b) inserting the hollow tube into a patient's body;
(c) advancing the inner expandable body relative to the distal end of the hollow tube such that the inner expandable body at least partially exits the hollow tube;
(d) expanding the inner expandable body against the outer expandable body a first time to deliver a first portion of the therapeutic agent;
(e) collapsing the inner expandable body and retracting the inner expandable body back into the hollow tube; and
(f) expanding the inner expandable body against the outer expandable body a second time to deliver a second portion of the therapeutic agent.

19. The method of claim 18, wherein the inner expandable body is advanced partially out of the hollow tube to a first distance from the distal end of the hollow tube, and further comprising:
repositioning the hollow tube; and
advancing the inner expandable body out of the hollow tube to a second distance from the distal end of the hollow tube, the second distance being greater than the first distance.

20. The method of claim 18, further comprising:
rotating the inner expandable body; and
advancing the inner expandable body such that the inner expandable body at least partially exits the hollow tube.

21. The method of claim 18, wherein the medical device further comprises at least two different types of capsules that are carried by the outer expandable body, the therapeutic agent being contained inside the capsules;
wherein the first expansion of the inner expandable body applies a first compressive force against a first type of capsules to release the therapeutic agent from the first type of capsules; and
wherein the second expansion of the inner expandable body applies a second compressive force against a second type of capsules to release the therapeutic agent from the second type of capsules.

* * * * *